US011123567B2

(12) United States Patent
Kuang

(10) Patent No.: US 11,123,567 B2
(45) Date of Patent: Sep. 21, 2021

(54) ANTENNA APPARATUS FOR USE WITH MEDICAL IMPLANTS

(71) Applicant: ADVANCED BIONICS AG, Staefa (CH)

(72) Inventor: Wensheng Vincent Kuang, Valencia, CA (US)

(73) Assignee: Advanced Bionics AG, Staefa (CH)

( * ) Notice: Subject to any disclaimer, the term of this patent is extended or adjusted under 35 U.S.C. 154(b) by 49 days.

(21) Appl. No.: 15/844,519

(22) Filed: Dec. 16, 2017

(65) Prior Publication Data

US 2018/0221673 A1    Aug. 9, 2018

Related U.S. Application Data

(60) Provisional application No. 62/455,727, filed on Feb. 7, 2017.

(51) Int. Cl.
*A61N 1/36* (2006.01)
*A61N 1/372* (2006.01)
*H04R 25/00* (2006.01)

(52) U.S. Cl.
CPC ..... *A61N 1/37229* (2013.01); *A61N 1/36038* (2017.08); *H04R 25/554* (2013.01); *H04R 25/603* (2019.05); *H04R 25/609* (2019.05); *H04R 25/65* (2013.01); *H04R 2225/021* (2013.01); *H04R 2225/51* (2013.01); *H04R 2225/57* (2019.05); *H04R 2225/67* (2013.01)

(58) Field of Classification Search
CPC ............ A61N 1/37229; A61N 1/36038; H04R 25/60; H04R 25/65; H04R 25/554; H04R 2225/51; H04R 2225/021; H04R 2225/67
See application file for complete search history.

(56) References Cited

U.S. PATENT DOCUMENTS

| | | | |
|---|---|---|---|
| 4,631,511 A | 12/1986 | Sylvester, Jr. et al. | |
| 5,500,632 A | 5/1996 | Halser | |
| 5,525,871 A | 6/1996 | Bray et al. | |
| 7,973,635 B2 | 7/2011 | Baarman et al. | |
| 8,666,491 B2 | 3/2014 | Chen et al. | |
| 2011/0009924 A1* | 1/2011 | Meskens | A61N 1/36036 607/57 |
| 2015/0115732 A1 | 4/2015 | Zabaco | |
| 2016/0163445 A1 | 6/2016 | Bertels | |
| 2016/0213936 A1* | 7/2016 | Heerlein | A61N 1/37229 |
| 2017/0040694 A1* | 2/2017 | Singh | H01F 27/38 |

FOREIGN PATENT DOCUMENTS

| | | | |
|---|---|---|---|
| WO | WO2014/049448 A2 | 4/2014 | |
| WO | WO2015/005777 A2 | 1/2015 | |

\* cited by examiner

*Primary Examiner* — Mallika D Fairchild
(74) *Attorney, Agent, or Firm* — Henricks Slavin LLP

(57) ABSTRACT

An antenna apparatus having a first coil including at least one turn on at least one first-coil substrate and a second coil including at least one turn on at least one second-coil substrate. The first and second coils are electrically connected to one another in parallel.

22 Claims, 6 Drawing Sheets

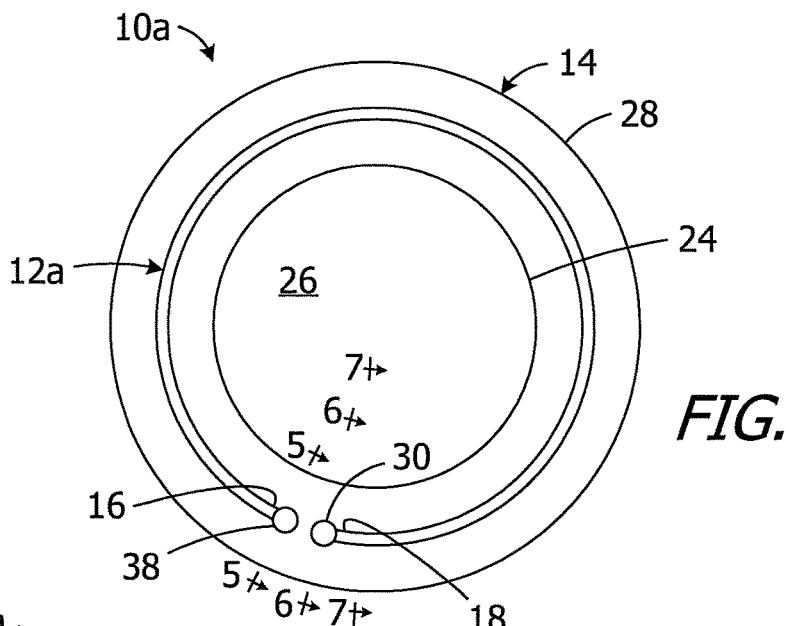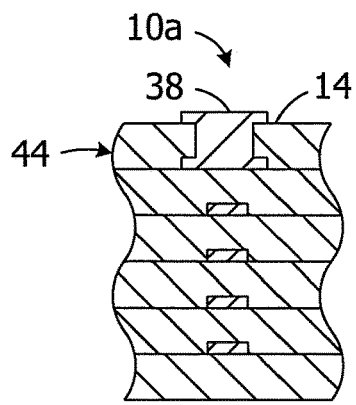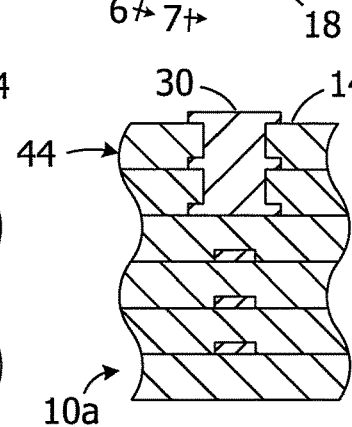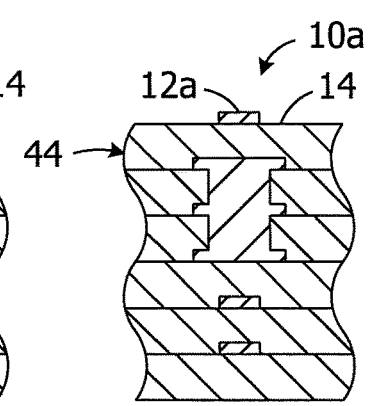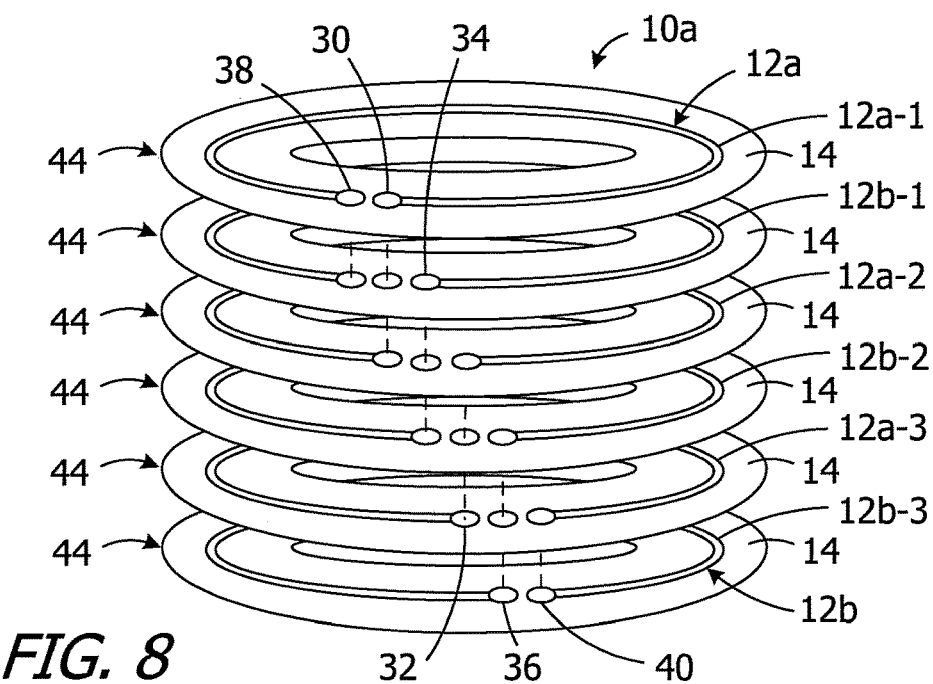

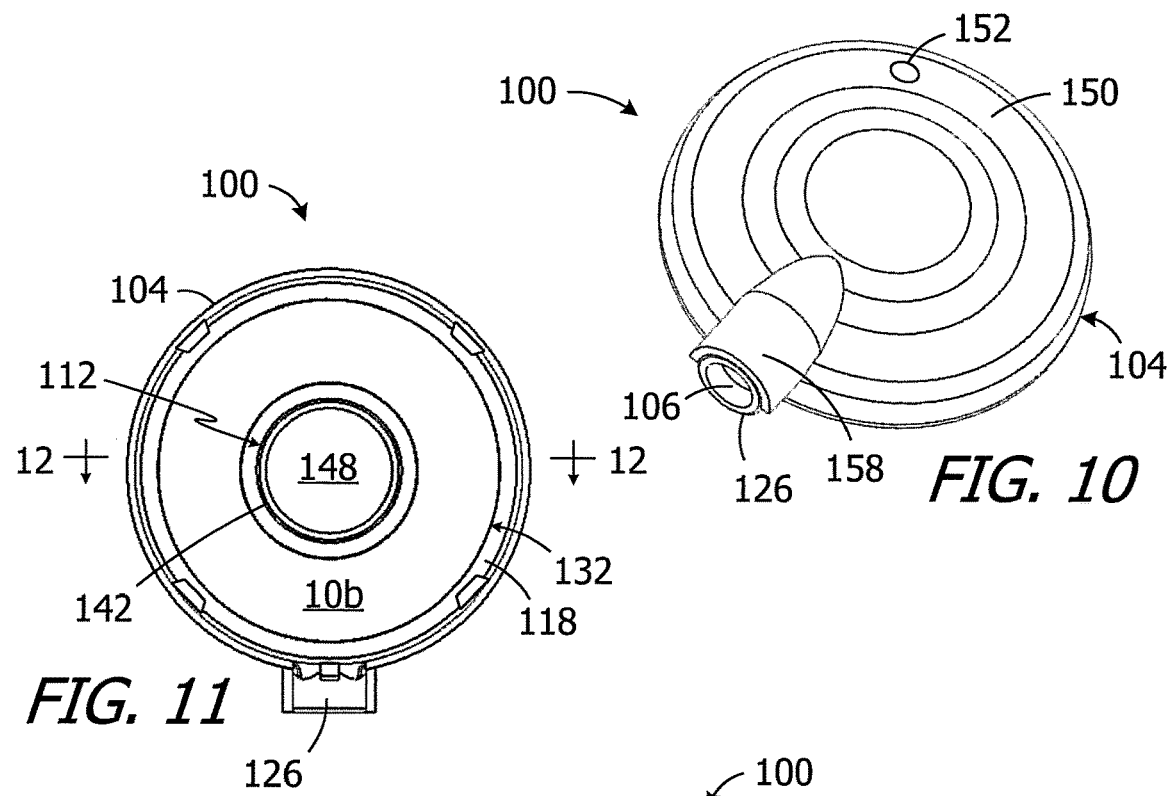
FIG. 10
FIG. 11
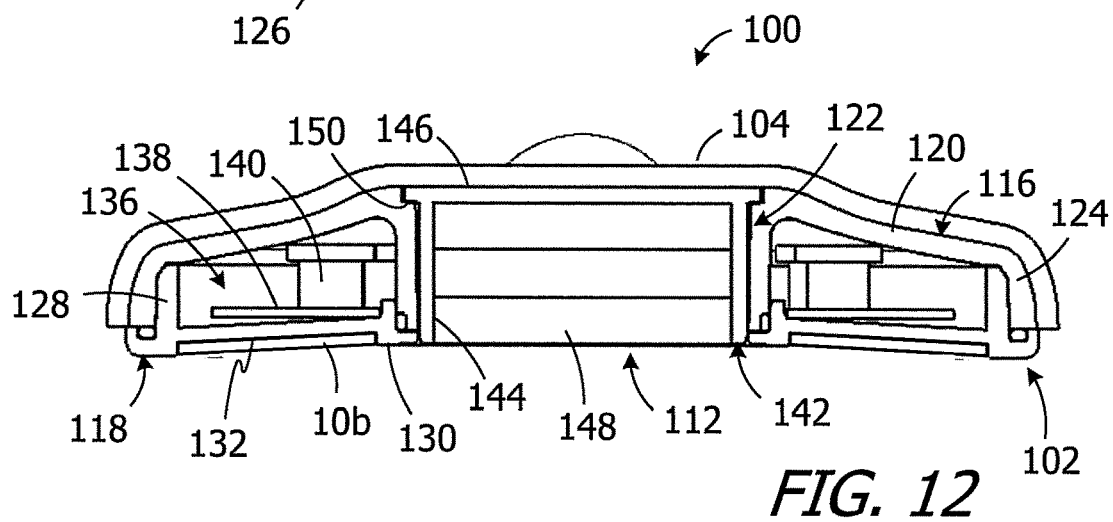
FIG. 12
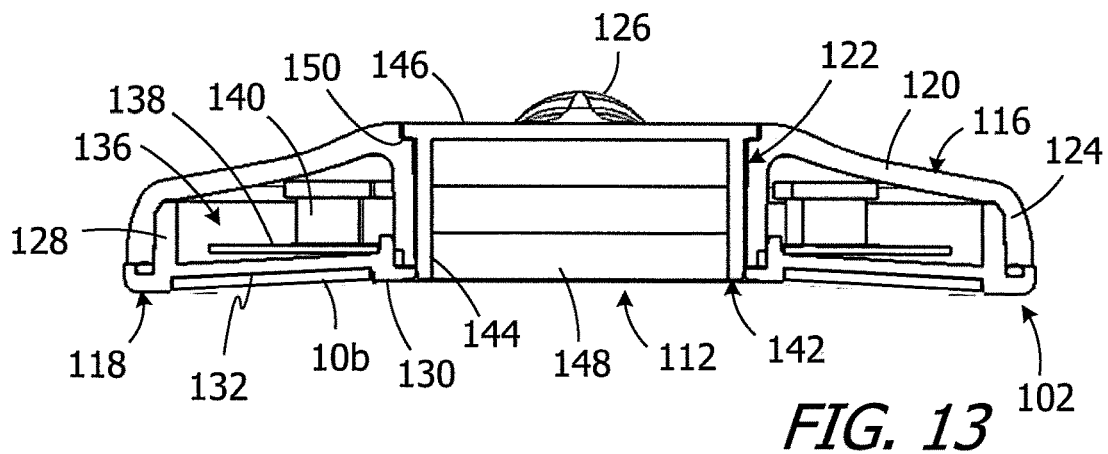
FIG. 13

ANTENNA APPARATUS FOR USE WITH MEDICAL IMPLANTS

CROSS-REFERENCE TO RELATED APPLICATIONS

This application claims priority to U.S. Prov. App. Ser. No. 62/455,727, filed Feb. 7, 2017, which is incorporated herein by reference.

BACKGROUND

1. Field

The present disclosure relates generally to transcutaneously powered medical implants.

2. Description of the Related Art

Inductive links are commonly used to transmit power and data to implanted medical devices such as, for example, prosthetic devices including cochlear implants and retinal implants, cardiac pacemakers, implantable defibrillators, recording devices, and neuromuscular stimulators. The implanted devices include (or are connected to) an internal antenna, and an external antenna is positioned over the internal antenna. Power and in some instances data is supplied to the implanted devices by way of the inductive link between the antenna.

In the exemplary context of implantable cochlear stimulation ("ICS") systems, which include an external sound processor as well as a cochlear implant with an electrode array within the cochlea, the external antenna may be carried by a headpiece that is connected to the external sound processor. The sound processor transmits power and stimulation data (e.g., a pulse sequence having varying pulse widths, rates and/or amplitudes) through a power modulation scheme to the antenna of the cochlear implant by way of an inductive link. Electrical stimulation current is applied to varying electrode combinations to create a perception of sound. The electrode array may, alternatively, be directly inserted into the cochlear nerve without residing in the cochlea. A representative ICS system is disclosed in U.S. Pat. No. 5,824,022, which is entitled "Cochlear Stimulation System Employing Behind-The-Ear Sound processor With Remote Control" and incorporated herein by reference in its entirety. Examples of commercially available ICS sound processors include, but are not limited to, the Advanced Bionics™ Harmony™ BTE sound processor, the Advanced Bionics™ Naida™ BTE sound processor and the Advanced Bionics™ Neptune™ body worn sound processor.

The present inventors have determined that conventional antennas are susceptible to improvement. For example, the present inventor has determined that it would be desirable to provide antennas with relatively low rates of energy loss that that can be manufactured using conventional manufacturing techniques.

SUMMARY

An antenna apparatus having a first coil including at least one turn on at least one first-coil substrate and a second coil including at least one turn on at least one second-coil substrate. The first and second coils are electrically connected to one another in parallel. The present inventions also include, for example, cochlear implant headpieces with such an antenna apparatus. The present inventions also include systems with a sound processor, cochlear implant headpieces with such an antenna apparatus, and a cochlear implant.

There a number of advantages with such apparatus, headpieces and systems. For example, the present antennas have relatively low rates of energy loss that that can be manufactured using conventional manufacturing techniques.

The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

FIG. 4 is a plan view of an antenna apparatus in accordance with one embodiment of a present invention.

FIG. 5 is a section view taken along line 5-5 in FIG. 4.

FIG. 6 is a section view taken along line 6-6 in FIG. 4.

FIG. 7 is a section view taken along line 7-7 in FIG. 4.

FIG. 8 is an exploded view of the antenna apparatus illustrated in FIG. 4.

FIG. 10 is a perspective view of a headpiece in accordance with one embodiment of a present invention.

FIG. 11 is a bottom view of the headpiece illustrated in FIG. 10.

FIG. 12 is a section view taken along line 12-12 in FIG. 11.

FIG. 13 is a section view taken along line 12-12 in FIG. 11 with the headpiece cap removed.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions.

Figure 1:
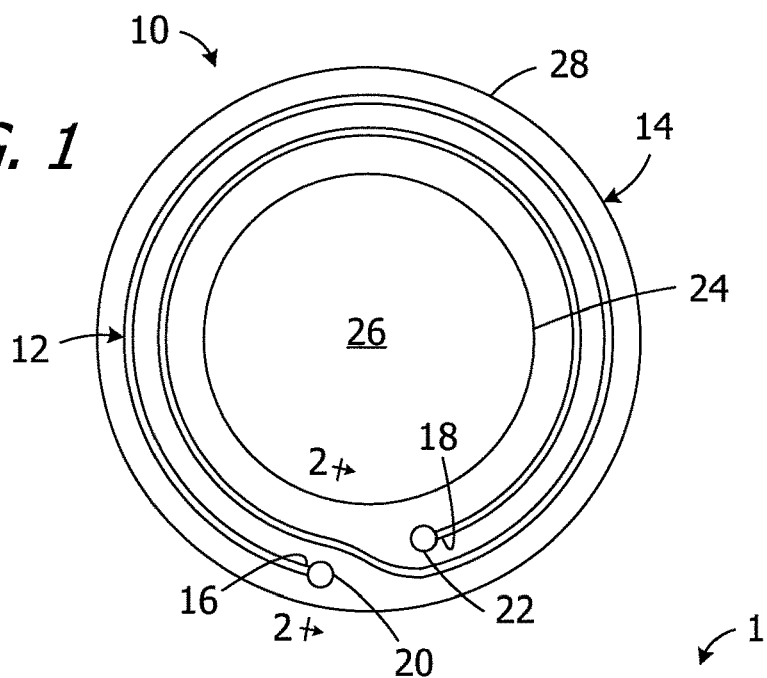
FIG. 1 is a plan view of an antenna apparatus in accordance with one embodiment of a present invention.
Figure 2:
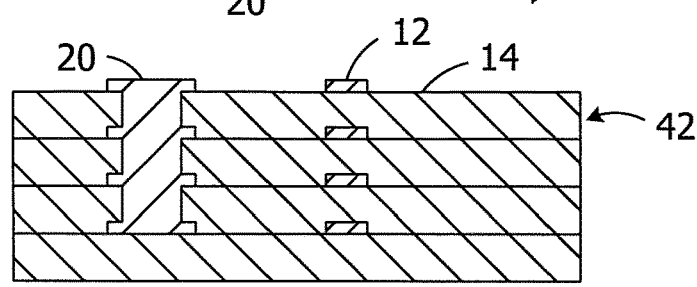
FIG. 2 is a section view taken along line 2-2 in FIG. 1.
Figure 3:
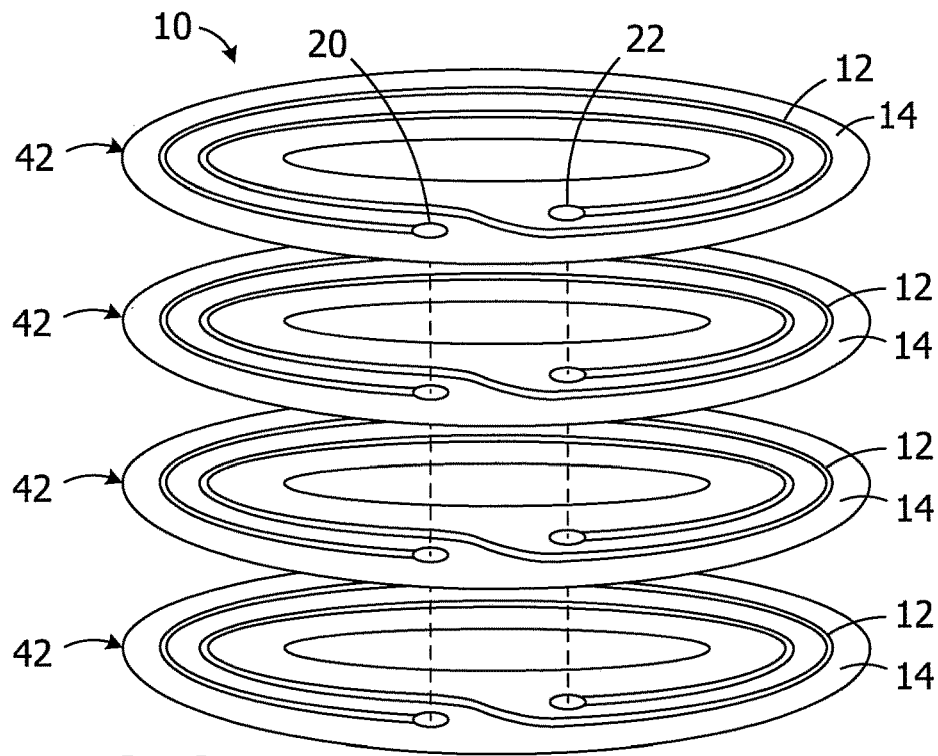
FIG. 3 is an exploded view of the antenna apparatus illustrated in FIG. 1.

As illustrated for example in FIGS. 1-3, an antenna apparatus 10 in accordance with one embodiment of at least some of the present inventions includes a plurality of coils 12 that are respectively carried on a plurality of insulating substrates 14. The coils 12 are electrically connected to one another in parallel. To that end, each coil 12 includes first and second ends (or "extremities") 16 and 18. The coils 12 are oriented relative to one another such that the first ends 16 are aligned with one another and the second ends 18 are aligned with one another. The first ends 16 of the coils 12 are connected to conductive vias 20 that electrically connect the first ends to one another. The second ends 18 of the coils 12 are connected to conductive vias 22 that electrically connect the second ends to one another. The exposed ends of the vias 20 and 22 may define pads that are used to connect the antenna apparatus 10 to, for example, the communication circuit of the associated device. In other implementations, the vias 20 and 22 may be connected to pads that are located on the surface of the top substrate 14 (in the illustrated orientation) or to a connection tab such as that discussed below with reference to FIG. 8A. Dashed lines are used in FIGS. 3 and 8 to illustrate the alignment of the various portions of the vias 20 and 22 associated with each substrate.

There are a number of advantages associated with the present antenna apparatus. By way of example, but not limitation, connecting the coils 12 to one another in parallel lowers the series resistance of the antenna apparatus 10 which, in turn, results in a higher Q factor at the resonant frequency. The Q factor is a unit-less indicator of efficiency, and a higher Q is indicative of a lower rate of energy loss for the conductor. In particular, $Q=\omega L/R$, where $\omega$=radian operating frequency, L=inductance and R=inductor's effective series resistance.

Although the present inventions are not limited to any particular coil and insulating substrate shapes, the exemplary antenna apparatus 10 is configured to form part of the headpiece 100 described below with reference to in FIGS. 10-15. To that end, the coils 12 are generally circular in overall shape and the insulating substrates 14 each include a circular inner edge 24 that defines a circular opening 26 and a circular outer edge 28. Depending upon the shape of the bottom of the headpiece, the antenna apparatus 10 may be flat or may have a frusto-conical shape that is achieved through the use of thermoforming or other suitable processes.

The coils 12 in the illustrated embodiment each include two turns. In other implementations, the number of turns may be increased or decreased. It should also be noted that only one via electrically connects the first coil ends 16 to one another, that only one via electrically connects the second coil ends 18 to one another, and that there are no additional vias (i.e., no vias other than vias 20 and 22) between the two ends in the embodiment illustrated in FIGS. 1-3. As such, there are only two vias in the exemplary antenna apparatus 10 illustrated in FIGS. 1-3. As used herein, "only one" means "one and no more than one" and "only two" means "two and no more than two." It should also be noted that when coils are referred to in a manner that distinguishes one from another, e.g., "first coil," "second coil," etc., the substrates on which some or all of the coils are located may be similarly distinguished, e.g., "first-coil substrate," "second-coil substrate," etc., for purposes of clarity.

The present antenna apparatus are also not limited to the antenna apparatus illustrated in FIGS. 1-3. By way of example, but not limitation, antenna apparatus in accordance with the present inventions may include multi-turn coils with at least some of the turns on different substrate layers. To that end, the exemplary antenna apparatus generally represented by reference numeral 10a in FIGS. 4-8 is similar to antenna apparatus 10 and similar elements are represented by similar reference numerals. Here, however, the antenna apparatus 10a includes first and second multi-turn coils 12a and 12b that are connected to one another in parallel. The coil 12a includes turns 12a-1 to 12a-3 and each of the turns is located on a separate substrate 14. The turns 12a-1 to 12a-3 are electrically connected to one another by vias 30 and 32 to form the coil 12a. Similarly, the coil 12b includes turns 12b-1 to 12b-3 and each of the turns is located on a separate substrate 14. The turns 12b-1 to 12b-3 are electrically connected to one another by vias 34 and 36 to form the coil 12b. It should also be noted that the vias 30-36 pass through a substrate without making electrical connection with the turn carried thereon (e.g., via 30 passes through the substrate 14 on which the turn 12b-1 is carried without making an electrical connection to turn 12b-1). The coils 12a and 12b are electrically connected to one another in parallel by vias 38 and 40.

In the implementation illustrated in FIGS. 4-8, the turns of coils 12a and 12b are arranged in alternating fashion such that the turns 12b-1 and 12b-2 are located between the turns 12a-1 to 12a-3, as shown in FIG. 8, and the turns 12a-2 and 12a-3 are located between the turns 12b-1 to 12b-3. In other implementations, the turns of coil 12a may be adjacent to one another (i.e., without any of the turns of coil 12b in between the turns of coil 12a) and the turns of coil 12b may be adjacent to one another (i.e., without any of the turns of coil 12a in between the turns of coil 12b). It should also be noted that in those instances where the antenna apparatus includes more than two multi-layer, multi-turn coils (e.g., three or more multi-layer, multi-turn coils), there may be layers (each with a substrate and at least one turn) of more than one coil between the layers (each with a substrate and at least one turn) of the same coil. For example, a layer from a second coil and a layer from a third coil may both be located between two layers from a first coil.

The exemplary antenna apparatus 10 and 10a are, as alluded to above, multi-layer structures, with each coil layer including a substrate and one or more turns. Although there are four coil layers 42 in the exemplary antenna apparatus 10 (FIGS. 1-3) and six coil layers 44 in the exemplary antenna apparatus 10a (FIGS. 4-8), the numbers may be increased or decreased to suit the intended application. Alternatively, or in addition, the number of turns in each layer may be increased or decreased and/or the number or turns in each coil may be increased or decreased. For example, each of the coil layers 44 (FIG. 8) may include two or more turns.

The multi-layer structures may be laminates formed in a manner similar to a printed circuit board. To that end, the exemplary coils 12-12b may be traces that are formed on the insulating substrates 14 by, for example, a patterning and etching process. The vias 20 and 22 that electrically connect the coils 12 of each layer 42 in FIG. 1-3, as well as the vias 30-40 that electrically connect the turns 12a-1 to 12b-3 and coils 12a and 12b in FIGS. 4-8, may be formed by, for example, conventional drilling and plating techniques. The vias may be filled (as shown) or unfilled. Suitable materials for the coils and vias include, but are not limited to, gold, silver and copper. The coils and vias may all be formed from the same material, or may be formed from different materials. The thickness of the coils 12-12b may range from about 0.01 mm to about 0.1 mm. Suitable materials for the insulating substrates 14 include dielectric materials such as, for example, liquid crystal polymer, sealed polyimide, glass-reinforced epoxy, polytetrafluoroethylene (PTFE) and other biocompatible materials. The thickness of the insulating substrates 14 may range from about 0.05 mm to about 0.5 mm. The total thickness of the assemblies 10 and 10*a* may range from about 0.2 mm to about 2.5 mm in some implementations, and is about 1.2 mm in the illustrated examples. As used herein in the context of an antenna apparatus, the term "about" means+/−5%. The top surface of the antenna apparatus 10 and 10*a* may be coated with a layer of liquid crystal polymer or other electrically insulating material.

Figure 8A:
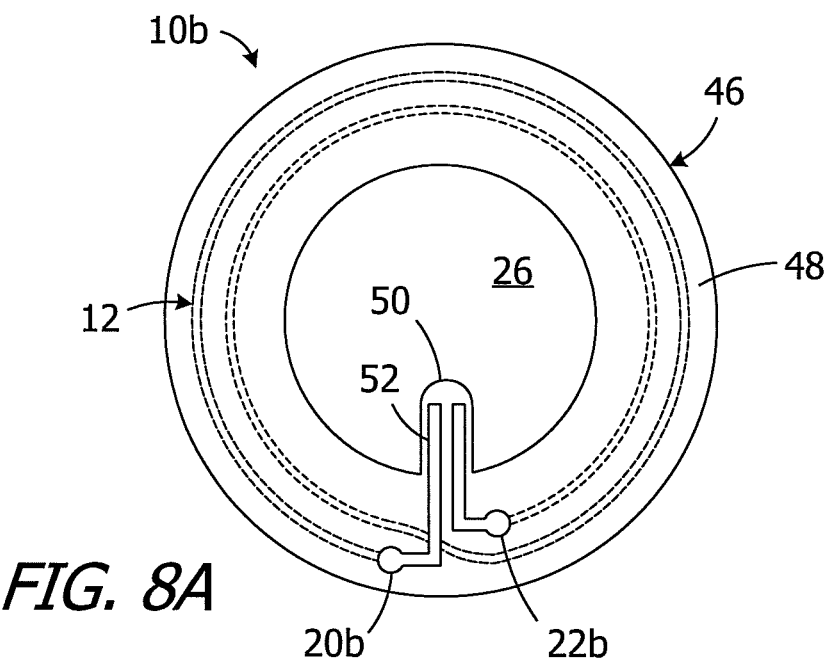
FIG. 8A is a plan view of an antenna apparatus in accordance with one embodiment of a present invention.

Another exemplary antenna apparatus is generally represented by reference numeral 10*b* in FIG. 8A. Antenna apparatus 10*b* is essentially identical to antenna apparatus 10 and similar elements are represented by similar reference numerals. Here, however, an insulating substrate 46, with an annular portion 48 and a tab 50, is positioned over the top substrate 14 (FIG. 2). A pair of conductors 52 on the surface of the substrate 48 may be connected to the coils by vias 20*b* and 22*b*. The connection tab may be used to electrically connect the antenna apparatus 10*a* to an apparatus that incorporates the antenna apparatus in the manner described below with reference to FIGS. 10-15. A substrate/tab arrangement may also be employed in conjunction with the antenna apparatus illustrated in FIGS. 4-8.

Figure 9:
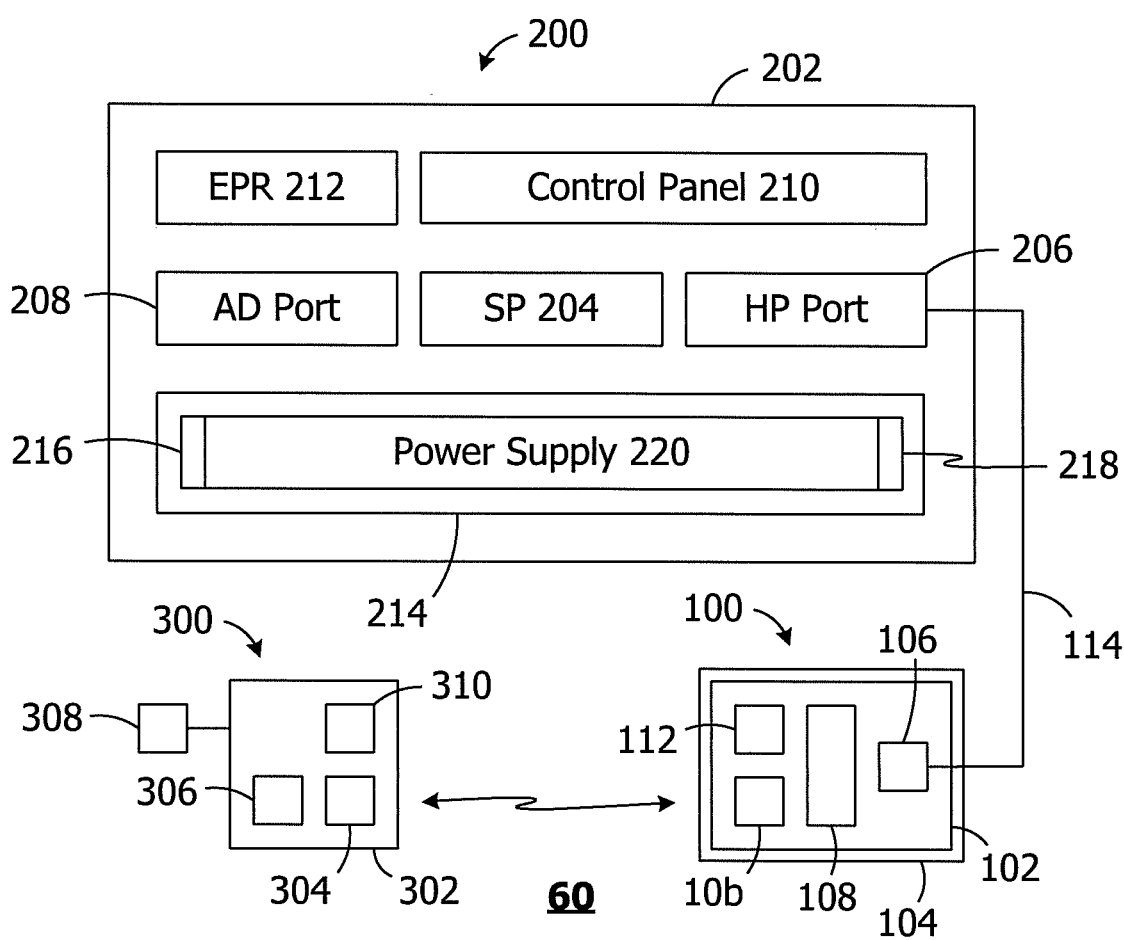
FIG. 9 is a functional block diagram of an ICS system in accordance with one embodiment of a present invention.

The present inventions have application in a wide variety of systems including, but not limited to, those that provide sound (i.e., either sound or a perception of sound) to the hearing impaired. One example of such a system is an ICS system where an external sound processor communicates with a cochlear implant and, accordingly, the present inventions may be discussed in the context of ICS systems. The present inventions are not, however, so limited. One example of an ICS system is the system generally represented by reference numeral 60 in FIG. 9. The exemplary ICS system 60 includes a headpiece 100, sound processor 200, and an implantable cochlear simulator (or "cochlear implant") 300.

The exemplary headpiece 100, which is described in greater detail below with reference to FIGS. 10-15, a housing 102 and a removable cap 104, as well as various components, e.g., a RF connector 106, a microphone 108, an antenna assembly 10*b* and a positioning magnet assembly 112, which are carried by the housing. The removable cap 104 may be omitted in some embodiments.

The exemplary sound processor 200 includes a housing 202 in which and/or on which various components are supported. Such components may include, but are not limited to, sound processor circuitry 204, a headpiece port 206, an auxiliary device port 208 for an auxiliary device such as a mobile phone or a music player, a control panel 210 (including, e.g., a volume knob and program switch), a Euro Plug receptacle 212 (for a Euro Plug such as that associated with the Phonak MLxi FM receiver), and a power supply receptacle 214 with electrical contacts 216 and 218 for a removable battery or other removable power supply 220 (e.g., rechargeable and disposable batteries or other electrochemical cells). A power button (not shown) may also be carried on the housing 202. The headpiece port 206 and auxiliary device port 208 may be connected to the sound processor circuitry 204 by way of, for example, a signal splitter/combiner (not shown) such as that found in the Platinum Sound Processor body worn unit from Advanced Bionics.

The headpiece 100 in the exemplary ICS system 60 may be connected to the headpiece port 206 by a cable 114. In at least some implementations, the cable 114 will be configured for forward telemetry and power signals at 49 MHz and back telemetry signals at 10.7 MHz. It should be noted that, in other implementations, communication between a sound processor and a headpiece and/or auxiliary device may be accomplished through wireless communication techniques.

The exemplary cochlear implant 300 includes a housing 302, an antenna 304, an internal processor 306, a cochlear lead 308 with an electrode array, and a positioning magnet (or magnetic material) 310. The antenna apparatus 10*b* and antenna 304 are respectively configured to communicate with one another by way of electromagnetic induction, radio frequencies, or any other wireless communication technology. The positioning magnet assembly 112 and positioning magnet (or magnetic material) 310 maintain the position of the headpiece antenna 10*b* over the cochlear implant antenna 304. Power and stimulation data may be transcutaneously transmitted from the antenna apparatus 10*b* to the antenna 304 by way of an inductive link.

During use, the microphone 108 picks up sound from the environment and converts the sound into electrical impulses, and the sound processor 200 filters and manipulates the electrical impulses and sends the processed electrical signals through the cable 114 to the antenna apparatus 10*b*. Electrical impulses received from an auxiliary device are processed in essentially the same way. The antenna 304 receives signals from the antenna apparatus 10*b* and sends the signals to the cochlear implant internal processor 306, which modifies the signals and passes them through the cochlear lead 308 to the electrode array. The electrode array may be wound through the cochlea and provides direct electrical stimulation to the auditory nerves inside the cochlea. This provides the user with sensory input that is a representation of external sound waves which were sensed by the microphone 108.

The exemplary sound processor 200 may be carried by the user in a variety of ways. By way of example, but not limitation, the sound processor 200 may be carried in the user's pocket, secured to a belt with a belt clip that is either part of housing 106 or a separate carrier, or placed in a harness that is configured to be worn by a small child.

Turning to FIGS. 10-13, and as noted above, the exemplary headpiece 100 includes a housing 102 and a removable cap 104 that may be secured to the housing. The housing 102 has a top portion 116 and bottom portion 118. The exemplary housing top portion 116 has a top wall 120, an aperture 122 for the magnet assembly 112, a housing microphone aperture (not shown), a side wall 124, and a connector tube 126 in which the connector 106 is located. The exemplary bottom portion 118 has a side wall 128 and a bottom wall 130 that extends slightly beyond the side wall. The bottom wall 130 is concave and includes an indentation (or recess) 132 for antenna assembly 10*b* that is secured to the bottom wall. The indentation extends upwardly from the concave bottom-most surface of the bottom wall 130. Adhesive bonding, or any other suitable bonding technique may be employed.

The exemplary housing 102 has an internal volume 136, defined by the top and bottom portions 116 and 118, in which the microphone 108 and a main printed circuit board ("main PCB") 138 are positioned. In the illustrated implementation, all of electronic components 140 (with the exception of the connector 106, microphone 108, and antenna 10*b*) are carried on the main PCB 138. Components 140 include capacitors, resistors and inductors. The connector 106 and microphone 108 may be connected to the main PCB 138 by, for example, connector wires and microphone wires (not shown) that are soldered to the main PCB. During assembly, the antenna apparatus 10*b* may be connected to the main PCB 138 by bending the connection tab 50 (FIG. 8A), inserting the tab 50 into the internal volume 136 by way of an aperture (not shown) in the housing bottom portion 118, and then soldering the conductors 52 to the main PCB 138.

The exemplary magnet assembly 112 includes a magnet housing 142, with a tubular member 144 and an end wall 146 that projects radially outward of the tubular member, and a plurality of magnets 148 located within the tubular member. The bottom surfaces of the tubular member 144 and bottom magnet 148 are aligned with one another. The magnets 148 may be secured to the tubular member 144 with a press-fit, adhesive, or any other suitable instrumentality. Although there are three magnets 148 in the assembly 112, this number may be increased or decreased to suit particular applications as is discussed below with reference to FIGS. 15 and 16. The edge of the end wall 146 rests within an indentation 150 in the housing top portion 116 that extends around the top end of the aperture 122, thereby limiting the downward movement of the magnet assembly 112. Upward movement is limited by the removable cap 104. As such, the magnet assembly 112 is held in place when the cap 104 is secured to the housing 102 (FIG. 12) and may be removed from the aperture 122 when the cap 104 is removed (FIG. 13). The housing 102 and magnet assembly 112 are also respectively configured such that the bottom surfaces of the housing bottom wall 130, the antenna assembly 10b, the bottom magnet 148, and the tubular member 144 are aligned with one another in the manner shown to form the concave bottom surface of the headpiece 100. In some instances, a thin biocompatible coating may be applied to the bottom surface of the bottom magnet 148.

Figure 14:
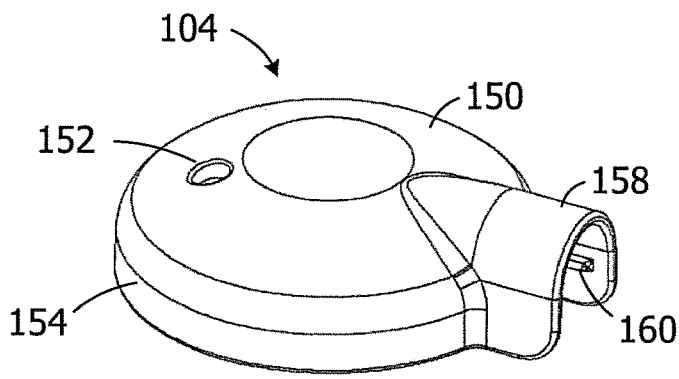
FIG. 14 is a perspective view of a headpiece cap in accordance with one embodiment of a present invention.
Figure 15:
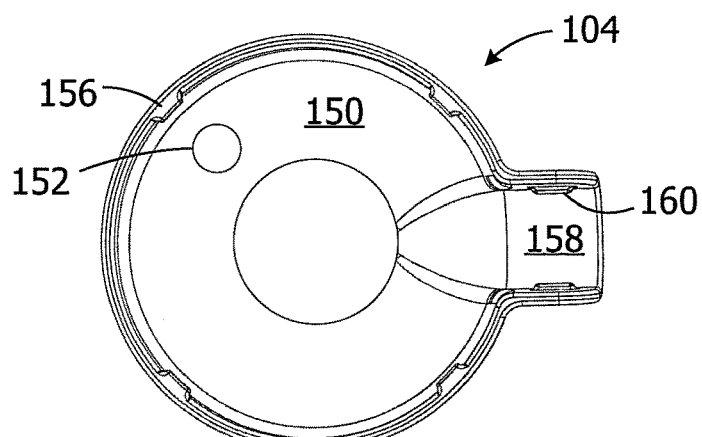
FIG. 15 is a bottom view of the headpiece cap illustrated in FIG. 14.

The removable cap 104 in the illustrated embodiment may be connected to and then removed from the housing 102, i.e., the cap may be removably connected to the housing. Referring to FIGS. 14 and 15, the exemplary cap 104 includes a top wall 150 with a sound port 152 that aligns with the microphone aperture (not shown) in the housing 102, a side wall 154 with a plurality of latches 156, and a connector hood 158 with a pair of latches 160. The respective configurations of the housing 102 and cap 104 allow the cap to be snap fit onto the housing and removed from the housing. In particular, the cap latches 156 will be aligned with housing latch indentations (not shown) when the housing 102 and cap 104 are oriented in the manner illustrated in FIGS. 10 and 11.

Additional information concerning headpieces that can accommodate the antenna assemblies described above may be found in US Pat. Pub. No. 2016/0213936, which is incorporated herein by reference.

Figure 16:
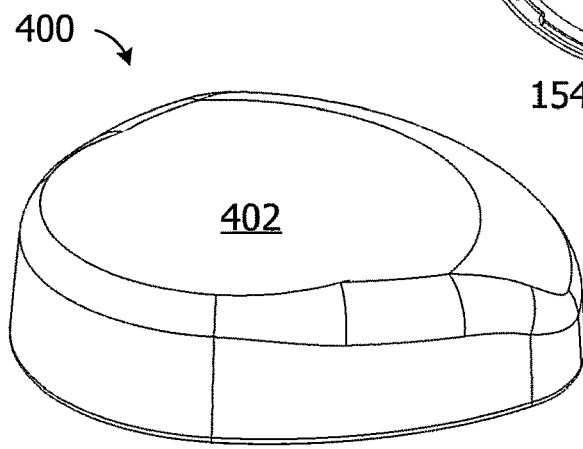
FIG. 16 is a perspective view of a headpiece in accordance with one embodiment of a present invention.
Figure 17:
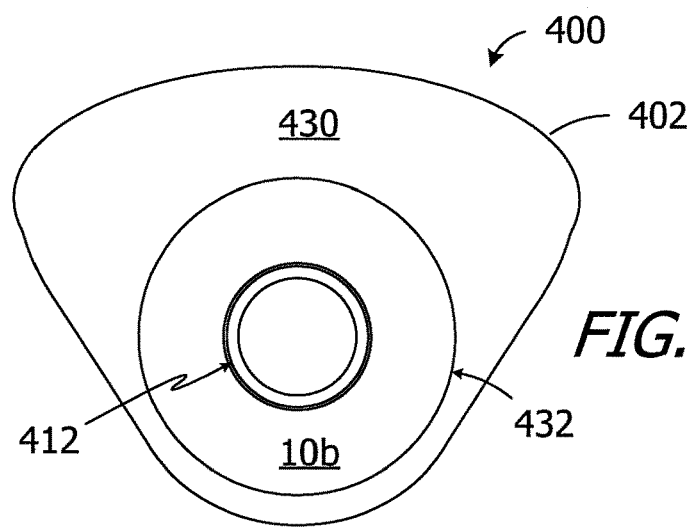
FIG. 17 is a bottom view of the headpiece illustrated in FIG. 16.
Figure 18:
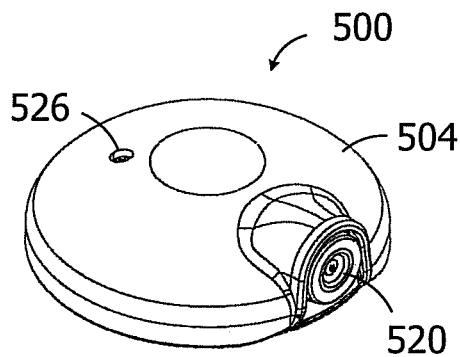
FIG. 18 is a perspective view of a headpiece in accordance with one embodiment of a present invention.
Figure 19:
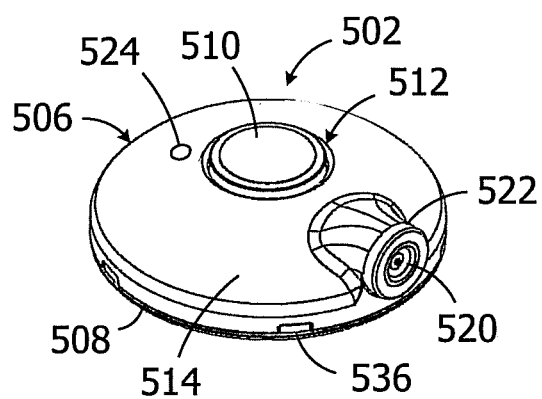
FIG. 19 is a perspective view of a portion of the headpiece illustrated in FIG. 18.
Figure 20:
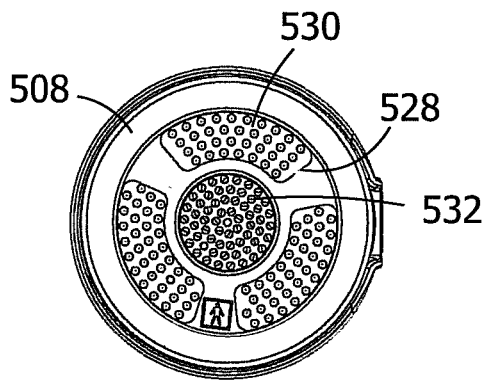
FIG. 20 is a bottom view of the headpiece illustrated in FIG. 18.

The present inventions are also applicable to headpieces that include all of the external components of a cochlear implant system. In addition to the aforementioned headpiece antenna coil and microphone, such headpieces also include sound processors and power supplies. By way of example, but not limitation, the headpiece 400 illustrated in FIGS. 16 and 17 is essentially identical to one of the headpieces illustrated and described in U.S. Pat. No. 8,811,643, which is incorporated herein by reference, but for the location of the headpiece antenna and associated modifications. The headpiece includes a housing 402 in which components (not shown) such as the sound processor, power supply and microphone are located. The flat bottom surface 430 of the housing 402 includes a recess 432 for a flat antenna assembly 10b. The housing 402 is also configured to accommodate a magnet assembly 412 or similar magnet arrangement. The bottom surface 430 may also be reconfigured so as to include a concave region for a concave antenna assembly. Other examples of headpieces that have all of the external components of a cochlear implant system, and may be modified to embody the present inventions, include the other headpieces illustrated and described in U.S. Pat. No. 8,811,643 as well as the headpiece illustrated and described in U.S. Pat. No. 8,270,647, which is also incorporated herein by reference.

Figure 21:
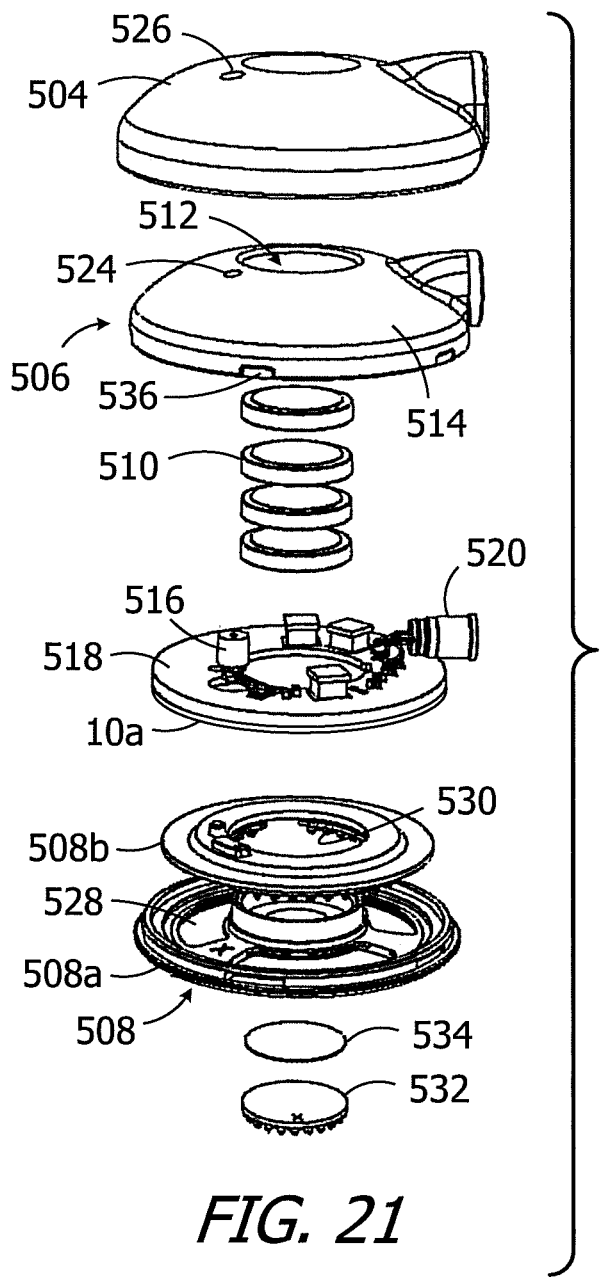
FIG. 21 is an exploded view of the headpiece illustrated in FIG. 18.

It should also be noted that the present antenna assemblies, such as assemblies 10 and 10a, may be mounted onto (or otherwise be an integral part of) the main PCB of the headpiece. To that end, and referring to FIGS. 18-21, the exemplary headpiece 500 includes a housing 502 and a removable cap 504 that may be secured to the housing. The housing 502 has a main portion 506 and a cover 508. A plurality of headpiece magnets 510, or a combination of magnets and non-magnetic spacers, are located within a cup 512 that extends to the top wall 514 of the main portion 506. The cap 504 keeps the magnets and spacers (if any) within the cup 512, and can be removed and reattached so that the magnets/spacers can be removed or added. The internal volume of the housing 502 includes a microphone 516 and a printed circuit board (PCB) 518 which carries the headpiece electronic components. An antenna assembly 10a (FIG. 21) may be mounted on, or may otherwise be an integral part of, the PCB 518. A connector 520, such as a RF connector, is connected to the PCB 518 and extends through a tube 522 on the housing main portion 506. The housing 502 and cap 504 also include microphone ports 524 and 526 that are aligned with the microphone 516. A shield (not shown) may be positioned over the port 526 on the inner surface of the cap 504.

The housing cover 508 includes a first portion 508a with apertures 528 and a second portion 508b with friction pads 530 that extend through the apertures. A circular friction pad 532 may be adhered to the bottom surface of the cover 508 with a double-sided adhesive mounting device 534. The exemplary friction pads 530 and 532 facilitate retention of the headpiece in the desired location over hair and sweat. It should also be noted that, if desired, a magnet may be adhered to the bottom surface of the cover 508 in place of the friction pad 532. The housing cover 508 also includes a plurality of latch indentations 536 that are engaged by a corresponding plurality of latches (not shown) on the cap 504 when the cap is positioned over the housing 502 in the manner illustrated in FIG. 18.

Although the inventions disclosed herein have been described in terms of the preferred embodiments above, numerous modifications and/or additions to the above-described preferred embodiments would be readily apparent to one skilled in the art. The inventions also include any combination of the elements from the various species and embodiments disclosed in the specification that are not already described. It is intended that the scope of the present inventions extend to all such modifications and/or additions and that the scope of the present inventions is limited solely by the claims set forth below.

I claim:

1. An antenna apparatus, comprising:
a first coil, including at least one turn and first and second ends, on at least one first-coil substrate; and
a second coil, including at least one turn and first and second ends, on at least one second-coil substrate;
wherein
the first ends of the first and second coils are electrically connected to one another by a first via that extends through the first-coil substrate from the first end of the first coil to the first end of the second coil, and the second ends of the first and second coils are electrically connected to one another by a second via that extends through the first-coil substrate from the second end of the first coil to the second end of the second coil, thereby electrically connecting the first and second coils to one another in parallel; and the first and second vias are the only two vias that connect the first and second coils to one another.

2. An antenna apparatus as claimed in claim 1, wherein
the first coil includes at least two turns on a single first-coil substrate; and
the second coil includes at least two turns on a single second-coil substrate.

3. An antenna apparatus as claimed in claim 1, wherein
the first coil includes at least a first turn on a first first-coil substrate and a second turn on a second first-coil substrate; and
the second coil includes at least a first turn on a first second-coil substrate and a second turn on a second second-coil substrate.

4. An antenna apparatus as claimed in claim 3, wherein
the first second-coil substrate is located between the first and second first-coil substrates;
the antenna apparatus further comprises a via that extends through the first second-coil substrate at a location spaced apart from the first turn of the second coil; and
the first and second turns of the first coil are electrically connected by the via.

5. An antenna apparatus as claimed in claim 1, wherein the first and second coils comprise first and second traces formed from a material selected from the group consisting of gold, silver and copper.

6. An antenna apparatus as claimed in claim 1, wherein the at least one first-coil substrate and the at least one second-coil substrate formed from a dielectric material selected from the group consisting of liquid crystal polymer, sealed polyimide, glass-reinforced epoxy, and polytetrafluoroethylene (PTFE).

7. An antenna apparatus as claimed in claim 1, wherein the antenna apparatus defines a total thickness that is greater than or equal to 0.2 mm and is less than or equal to 2.5 mm.

8. An antenna apparatus as claimed in claim 1, wherein the first-coil substrate and the second coil substrate define respective outer edges;
the first and second ends of the first coil are located inward of the outer edge of the first-coil substrate; and
the first and second ends of the second coil are located inward of the outer edge of the second-coil substrate.

9. A headpiece for use with a cochlear implant having an antenna, the headpiece comprising:
a housing;
a circuit board located within the housing; and
an antenna apparatus as claimed in claim 1, configured to communicate with the cochlear implant antenna, that is located on or within the housing with the first and second coils operably connected to the circuit board.

10. A headpiece as claimed in claim 9, wherein
the housing includes a bottom wall; and
the antenna apparatus is mounted on or embedded within the bottom wall.

11. A headpiece as claimed in claim 9, further comprising:
a magnet carried by the housing.

12. A headpiece as claimed in claim 9, wherein
the antenna apparatus is mounted on the circuit board.

13. A headpiece as claimed in claim 9, wherein
the antenna apparatus is integral with the circuit board.

14. A headpiece as claimed in claim 9, further comprising:
a sound processor within the housing.

15. A cochlear implant system, comprising:
a headpiece as claimed in claim 9;
a sound processor; and
a cochlear implant including a cochlear implant antenna.

16. A cochlear implant system as claimed in claim 15, wherein
the sound processor is located within the headpiece.

17. A cochlear implant system as claimed in claim 15, wherein
the sound processor comprises a behind-the-ear sound processor.

18. A cochlear implant system as claimed in claim 15, wherein
the sound processor comprises a body worn sound processor.

19. A system, comprising:
an external antenna apparatus including
a first coil, including at least one turn and first and second ends, on at least one first-coil substrate, and
a second coil, including at least one turn and first and second ends, on at least one second-coil substrate, wherein
the first ends of the first and second coils are electrically connected to one another by a first via that extends through the first-coil substrate and the second ends of the first and second coils are electrically connected to one another by a second via that extends through the first-coil substrate, thereby electrically connecting the first and second coils to one another in parallel; and
the first and second vias are the only two vias that connect the first and second coils to one another; and
an implantable medical device including an implant antenna.

20. A system as claimed in claim 19, wherein
the implantable medical device comprises a cochlear implant including a cochlear implant antenna.

21. A system as claimed in claim 20, wherein
the external antenna apparatus is in communication with a sound processor.

22. A system as claimed in claim 19, wherein
the first-coil substrate and the second coil substrate define respective outer edges;
the first and second ends of the first coil are located inward of the outer edge of the first-coil substrate; and
the first and second ends of the second coil are located inward of the outer edge of the second-coil substrate.

* * * * *